United States Patent
Shevchenko et al.

(10) Patent No.: US 8,500,957 B2
(45) Date of Patent: *Aug. 6, 2013

(54) ENHANCED METHOD FOR MONITORING THE DEPOSITION OF ORGANIC MATERIALS IN A PAPERMAKING PROCESS

(75) Inventors: Sergey M. Shevchenko, Aurora, IL (US); Michael J. Murcia, DeKalb, IL (US)

(73) Assignee: Nalco Company, Naperville, IL (US)

( * ) Notice: Subject to any disclaimer, the term of this patent is extended or adjusted under 35 U.S.C. 154(b) by 277 days.

This patent is subject to a terminal disclaimer.

(21) Appl. No.: 12/907,478

(22) Filed: Oct. 19, 2010

(65) Prior Publication Data

US 2011/0073263 A1  Mar. 31, 2011

Related U.S. Application Data

(63) Continuation-in-part of application No. 11/846,920, filed on Aug. 29, 2007, now Pat. No. 7,842,165.

(51) Int. Cl.
*D21H 23/08* (2006.01)

(52) U.S. Cl.
USPC ........... 162/198; 162/263; 162/264; 162/191; 162/49

(58) Field of Classification Search
USPC ................. 162/198, 199, 263, 272, 274, 4, 5, 162/49, 191, 264; 73/61.45, 61.49, 61.61, 73/61.62, 61.75, 61.79, 64.53
See application file for complete search history.

(56) References Cited

U.S. PATENT DOCUMENTS

| | | | | |
|---|---|---|---|---|
| 3,266,291 | A * | 8/1966 | King, Jr. ...................... | 73/24.06 |
| 4,399,686 | A * | 8/1983 | Kindlund et al. ............ | 73/24.06 |
| 5,589,396 | A * | 12/1996 | Frye et al. ........................ | 436/73 |
| 6,357,278 | B1 * | 3/2002 | Sivavec et al. ............... | 73/24.01 |
| 7,449,086 | B2 * | 11/2008 | Gray et al. .................. | 162/181.6 |
| 7,842,165 | B2 * | 11/2010 | Shevchenko et al. ......... | 162/198 |
| 2006/0281191 | A1 * | 12/2006 | Duggirala et al. ............ | 436/178 |

* cited by examiner

*Primary Examiner* — Eric Hug
(74) *Attorney, Agent, or Firm* — Calfee, Halter & Griswold LLP

(57) ABSTRACT

A method for monitoring with enhanced sensitivity of the deposition of one or more organic materials dispersed in an aqueous medium in a papermaking process which includes measuring the rate of deposition of the organic materials from the aqueous medium onto a quartz crystal microbalance having a top side contacting with the aqueous medium coated with a layer containing a material with surface energy in the range from about 34 to about 49 dynes/cm2, and a second, bottom side isolated from the aqueous medium is disclosed. Additionally, a method for measuring the effectiveness of an inhibitor that decreases the deposition of the organic materials in a papermaking process is also disclosed.

14 Claims, 7 Drawing Sheets

ENHANCED METHOD FOR MONITORING THE DEPOSITION OF ORGANIC MATERIALS IN A PAPERMAKING PROCESS

PRIORITY INFORMATION

This is a continuation-in-part application of U.S. patent Ser. No. 11/846,920, filed Aug. 29, 2007 now U.S. Pat. No. 7,842,165.

FIELD OF THE INVENTION

This invention is in the field of papermaking. Specifically, this invention is in the field of monitoring organic deposit formation in a papermaking process.

BACKGROUND OF THE INVENTION

Organic materials, such as pitch, stickies, and tackles, are major obstacles in paper manufacturing because these materials when liberated during a papermaking process can become both undesirable components of papermaking furnishes and troublesome to the mill equipment, e.g. preventing proper operation of mechanical parts when these materials deposit on the mechanical parts. White pitch is a particular obstacle in the manufacture of paper and tissue using recycled fiber (mixed office waste, old corrugated containers, old newsprint) and coated broke. For paper grades, these non-polar, tacky contaminants, when liberated during processing repulping, can become both undesirable components of papermaking furnishes and troublesome deposits on the mill equipment, e.g. wires of the tissue machine.

Stickies and tackles are organic materials that do not have precise definitions; they are tacky substances contained in the pulp and process water system that deposit on paper/tissue machine clothing, cylinders, and/or rolls. They vary in chemical structure: natural wood pitch consists of fatty acids, fatty esters and rosin acids, while stickies and white pitch originating from synthetic additives (adhesives, coating binders, printing ink) contain styrene butadiene rubber, ethylene vinyl acetate, polyvinyl acetate, polyvinyl acrylate, polyvinyl butyral, polybutadiene, wax, alkyd resins, polyol acrylates, etc. However, they all are hydrophobic materials that do not have a strong affinity to metal surfaces that creates a problem in monitoring such microparticles (micro stickies are those that can pass the 0.10-0.15 mm screening slots) using a of conventional quartz crystal microbalance (QCM).

U.S. Patent Application Publication No. 2006/0281191 (Duggirala et al., assigned to Nalco Company) discloses using a quartz crystal microbalance (QCM) in monitoring of organic deposits. The disclosed method is not universal and cannot be used in a special case of highly hydrophobic microstickies because they do not accumulate on the metal surface.

A publication by Tsuji et al. (2006) claims a new method for measuring microstickies in deinked pulp processes using a QCM-D (quartz crystal microbalance with dissipation monitoring) technique. The samples were taken at the inlet and the outlet of flotation cells for white water in a deinking mill. The adsorption behavior of dissolved and colloidal substances (DCS) in white water onto the surfaces (hydrophilic Au and hydrophobic polystyrene) was monitored. However, the published results demonstrated a very poor response of the sensor, orders of magnitude lower than that observed when the technique proposed in the parent application. Tsuji et al. does not indicate whether the observed changes are caused by microstickies.

Deposition of organic materials on the surface of a quartz crystal microbalance sensor is known. However, due to the low affinity of a standard surface to hydrophobic organic materials, the rate of deposition is normally low.

Coating of the QCM surface to affect the rate of deposition, generally, is a known idea. Moreover, a polymer coating composition including an epoxy resin (the preferred coating in the parent application) was described, though with a different aim. However, the special method of coating developed here and the application of a specially designed polymer and a class of polymers, effectively providing a sensitizing coating for stickies monitoring using QCM is now identified.

Additionally, the hydrophobic materials in pulp slurries (pitch in virgin pulp, stickies in recycled furnish) are known to have relatively low surface energy; for stickies it is in the range 30-45 dynes/cm2, and, for example, the tack for pressure-sensitive adhesives (PSA) depends on the surface energy. Surface energy quantifies the disruption of intermolecular bonds that occurs when a surface is created. The surface energy may be defined as the excess energy at the surface of a material compared to the bulk An efficacious and enhanced method of monitoring the deposition of organic materials is thus desired. Furthermore, a method of monitoring the effectiveness of inhibitors that prevent/reduce deposition of organic materials in a papermaking process is also desired. Even further, a method of measuring microstickies in deinked pulp processes using a QCM technique is ultimately desired.

SUMMARY OF THE INVENTION

The present invention provides a method for monitoring the deposition of hydrophobic materials from a liquid or slurry comprising measuring the rate of deposition onto a coated quartz crystal microbalance.

The present invention further provides a method for monitoring the deposition of organic materials dispersed in an aqueous medium onto a quartz crystal microbalance. The quartz crystal microbalance has a top side in contact with the aqueous medium that is coated with a layer that contains a material having a surface energy of a particular range. The quartz crystal microbalance also has a bottom side that is isolated from the aqueous medium.

The present invention also provides a method for evaluation of stickies and related hydrophobic deposit control treatments in a papermaking process. The monitoring comprises the steps of measuring the rate of deposition of the at least one organic material from the aqueous medium onto a quartz crystal microbalance, adding an inhibitor that decreases the deposition of the at least one organic material from the aqueous medium, and re-measuring the rate of deposition of the at least one organic material from the aqueous medium onto the coated surface of the quartz crystal microbalance. The quartz crystal microbalanace has a top side that contacts the aqueous medium, the top side coated with a layer that contains a non-swelling epoxy resin or a silicone-containing polymer. The crystal quartz microbalance also has a bottom side that is isolated from the aqueous medium.

BRIEF DESCRIPTION OF THE DRAWINGS

The benefits and advantages of the present invention will become more readily apparent to those of ordinary skill in the relevant art after reviewing the following detailed description and accompanying drawings, wherein.

Figure 1:
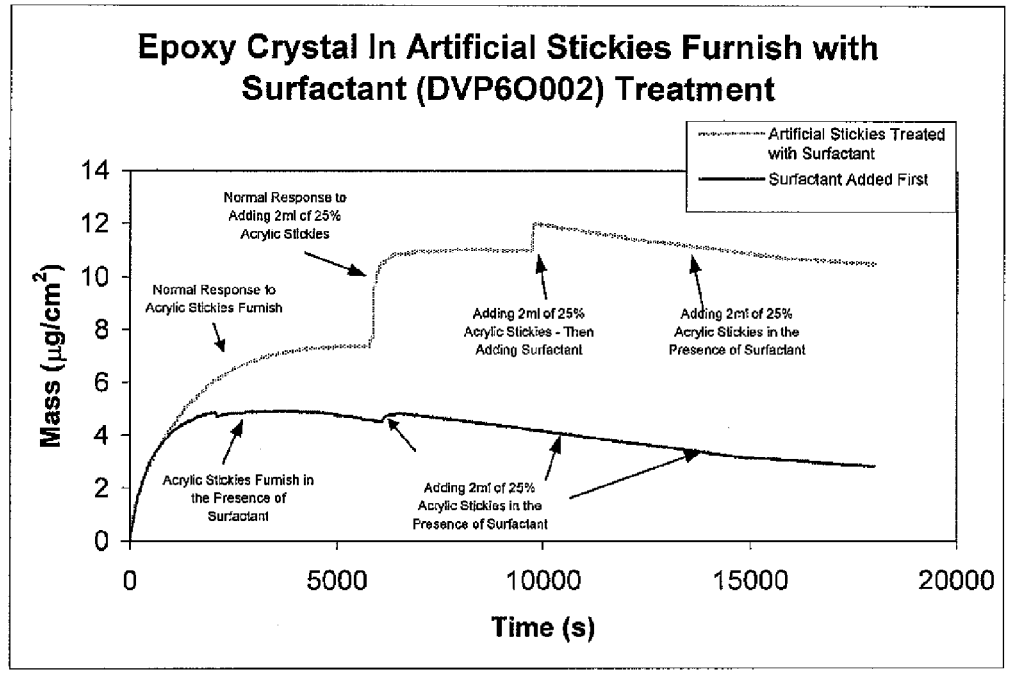
FIG. 1 is a graph that is related to Example 1.

DETAILED DESCRIPTION OF THE INVENTION a. Definitions

"Papermaking process" means a method of making any kind of paper products (e.g. paper, tissue, board, etc.) from pulp comprising forming an aqueous cellulosic papermaking furnish, draining the furnish to form a sheet and drying the sheet. The steps of forming the papermaking furnish, draining and drying may be carried out in any conventional manner generally known to those skilled in the art. The papermaking process may also include a pulping stage, i.e. making pulp from woody raw material and bleaching stage, i.e. chemical treatment of the pulp for brightness improvement.

"QCM" means quartz crystal microbalance.

"DRM" means deposit rate monitor (Nalco Company) described in Shevchenko, Sergey M.; Lu, Yu-Mei; Murcia, Michael J.; Rice, Laura E.; Mitchell, Carl; Novel concepts for monitoring and control of deposits in the pulp and paper mills; Proc. 64th Appita Annual Conference and Exhibition (2010), 267-272 and Shevchenko, Sergey M.; Duggirala, Prasad Y.; Deposit management for the bleach plant; IPPTA Journal (2010), 22(1), 135-140. A DRM contains a QCM. Both documents are herein incorporated by reference.

"SRM" means scale rate monitor. U.S. Pat. No. 6,375,829 and U.S. Pat. No. 6,942,782 describe Nalco's scale rate monitor, and are herein incorporated by reference. An SRM contains a QCM.

"RQCM" means research quartz crystal microbalance, which is commercially available from Maxtek, Inc., Cypress, Calif.

b. Preferred Embodiments

QCMs are known in the art of papermaking. DRMs, SRMs and RQCMs are examples of types of instruments using QCMs. In one embodiment, the top side of the quartz crystal microbalance is made up of one or more conductive materials selected from the group consisting of: platinum; titanium; silver; gold; lead; cadmium; diamond-like thin film electrodes with or without implanted ions; silicides of titanium, niobium, and tantalum; lead-selenium alloys; mercury amalgams; and silicone.

Coating the top side of a quartz crystal microbalance with a layer containing a non-swelling epoxy resin or a silicone containing polymer facilitates adhesion of organic deposits to the surface of the quartz crystal microbalance.

A non-swelling epoxy resin applied to a quartz crystal microbalance has the characteristic of not substantially swelling in an aqueous environment, e.g. aqueous medium in a papermaking process. One of ordinary skill in the art can determine whether a resin is non-swelling without undue experimentation.

Mutual adhesion of the surfaces of a sensor and target material is critical for the QCM monitoring. It is commonly thought that hydrophobic materials in pulp slurries, such as stickies in recycled furnish, are highly hydrophobic, have low surface energies, and therefore very hydrophobic, low-surface-energy surfaces must be used for their collection. This idea is behind some conventional coupon methods for macrostickies and the method used by Tsuji et al. Indeed, such materials have very low affinity towards metal surfaces. However, the better material choice for QCM coating is not the most hydrophobic but the materials having an intermediate hydrophobicity, similar in surface energies to pitch and stickies themselves. The better materials for QCM coating have a surface energy in the range of 34-49 dynes/cm$^2$.

In one embodiment, the resin is selected from the group consisting of a cresol-novolac epoxy resin; a phenol novolac epoxy resin; a bisphenol F (4,4'-, 2,4'- or 2,2'-dihydroxydiphenylmethanes or a mixture thereof) epoxy resin; a polynuclear phenol-glycidyl ether-derived resin; a tetraglycidyl-methylenedianiline-derived resin; a triglycidyl-p-aminophenol derived resin; a triazine-derived resin; and a hydantoin epoxy resin.

In another embodiment, the resin is derived from epichlorohydrin and 4,4'-dihydroxy-2,2-diphenylpropane (bisphenol A; may also contain 2,4'- or/and 2,2'-isomers).

In another embodiment, the resin contains an aromatic backbone, aliphatic backbone, cycloaliphatic backbone, or a heterocyclic backbone.

A silicone containing polymer can also be applied to the surface of a quartz crystal microbalance.

In one embodiment, the silicone containing polymer is selected from the group consisting of: silicone rubber, and room temperature vulcanizing silicone rubber.

A cellulose coating can also be applied to the surface of a quartz crystal microbalance.

A coupling agent may be utilized to facilitate the adhesion of the resin to the QCM surface.

In one embodiment, the coupling agent is 3-glycidoxypropyltrimethox-silane, which is available from Dow Corning® Corporation, as DOW CORNING Z-6040® SILANE. DOW CORNING Z-6040® SILANE is a heterobifunctional coupling agent.

In a further embodiment, DOW CORNING Z-6040® SILANE is prepared as a 0.1-0.5% solution in acidified water and applied to the active face of the crystal, and then after applying the silane, the crystal is dried at 104° C.-121° C., resulting in an epoxide functionalized surface that is covalently linked to the quartz crystal. The surface is then coated with a thin layer of epoxy.

The epoxy resin and silicone containing polymer may be applied to the QCM surface by various methods that would apparent to one of ordinary skill in the art.

In one embodiment, the epoxy resin or silicone containing polymer are applied to the QCM surface by a drop coating method or a spin coating method.

After the epoxy resin or silicone containing polymer is applied to the QCM surface, the epoxy resin and silicone containing polymer are hardened/cured.

The epoxy resin is hardened/cured by a curing agent. The type of curing agent utilized would be apparent to one of ordinary skill in the art without undue experimentation and is chosen so that the resin becomes a cured/hardened non-swelling resin.

The silicone containing polymer does not require a curing agent. The silicone containing polymer should be chosen so that it hardens subsequent to its application to the QCM surface. This can be determined without undue experimentation.

In one embodiment, the curing agent is selected from the group consisting of: short chain aliphatic polyamines; oxyalkylated short chain polyamines; long chain polyamine adducts; aromatic polyamines; polyaminoamides; and polythiols.

Various types and combinations of organic materials are in a papermaking process. The methodologies embodied in the present disclosure serve to monitor the deposition of one or more organic materials/combinations of organic materials.

In one embodiment, the organic materials are hydrophobic.

In a papermaking process, organic materials include natural and/or synthetic contaminants. Under the guise of synthetic contaminants, there are stickies and tackies. White pitch is a common term that correlates to stickies and tackies.

In one embodiment, the stickies are microstickies.

In another embodiment, the microstickies do not exceed approximately 0.10-0.15 mm in size.

In another embodiment, the stickies and tackies are components of printing ink.

In another embodiment, the stickies and tackies are selected from the group consisting of: adhesives; coating binders; styrene butadiene rubber; ethylene vinyl acetate; polyvinyl acetate; polyvinyl acrylate; polyvinyl butyral; polybutadiene; wax; alkyd resins; polyol acrylates; and sizing chemicals.

Under the guise of natural contaminants, there is natural wood pitch. Deposition of one or more organic materials may be monitored at various locations in the papermaking process.

In one embodiment, the monitoring occurs in a papermaking process at a location selected from the group consisting of: pulp processing; recycling; a refiner, a repulper; a bleaching chest; a deinking stage; a water loop; a headbox of a paper or tissue machine, and a combination thereof.

Papermaking processes encompassed by this invention include, but are not limited to, board production, and papermaking processes that involve recycled pulp and/or broke.

The aqueous medium in a papermaking process includes liquids and slurries. In one embodiment, the aqueous medium is a pulp slurry.

In order to reduce deposition of organic materials in a papermaking process, various types of inhibitors are added to the papermaking process. The inhibitors serve to reduce/eliminate deposition of unwanted organic materials in a papermaking process. For example, there are many anti-pitch or anti-stickies treatments that are currently employed to reduce deposition of the organic materials. Therefore by using the protocols of this invention, the efficacy of these inhibitors can be determined. More specifically, paper chemistry programs may be developed based upon information obtained from the monitoring procedures of this invention. Moreover, feedback protocols may be developed to provide not only monitoring but control of chemistry added to the papermaking process so that the process becomes more cost-efficient, more efficacious, and produces a better paper product.

EXAMPLES

The following techniques were in utilized in the experiments discussed below. The method for coating the crystals used in the DRM, SRM and RQCM experiments was based on spin coating the epoxy resin onto the crystal when removed from the sensor. The crystals were cleaned of any organic contaminants by washing with acetone followed by 0.5N HCl and deionized water ("DI") water. The clean crystals were dried under a flow of nitrogen and fitted to a spin coater. The two-part epoxy resin was homogenized in acetone or tetrahydrofuran (THF) at a concentration of 10% by wt. The epoxy solution was deposited onto the top side of the crystal, covering the entire surface. The crystal was spun at 2500 revolutions per minute (RPM) for 50 seconds, yielding a thin layer of epoxy, which was allowed to cure at room temperature for three days.

In cases where the crystal was fixed in the instrument, a different approach was used to apply the epoxy coating. The surface of the crystal was cleaned in the same manner as the crystals for the DRM, SRM and RQCM, but the homogenized, two part epoxy was further diluted in acetone or THF to a concentration of 5% by wt. Roughly 100 microliters of this solution was dropped onto the surface of the crystal from approximately six inches above the crystal's surface to promote spreading of the solution. After rapid evaporation of the acetone, the resulting thin layer of epoxy deposited onto the crystal's surface was allowed to cure at room temperature for three days.

Protocol A

To simulate deposition, model stickies suspension consisting of emulsified acrylate microspheres was added to a suspension of pulp at 0.3 to 3% consistency. The effect of pulp consistency in the tested system on the rate of deposition is an important question related to the development of monitoring techniques for mill applications. The standard DRM or SRM batch system, which employs a magnetic stirrer, works well when the pulp is present at very low consistency, but it is not suitable to analyze higher-consistency slurries. This system was modified by using a wide propeller stirrer connected to a motor. The cell was firmly attached to a stand, and the stirrer was reaching the cell through a slot in the lid normally used by the heating rod. This system provided uniform stirring at 400 RPM of the pulp of up to 5% consistency.

An emulsion of microstickies consisting of an acrylic adhesive was pre-mixed into the stirring pulp slurry at a concentration of 0.25% by wt. of slurry. The mass deposition onto the crystal surface was then monitored with the SRM as a function of time. The effect of spiking a system with this adhesive emulsion during an ongoing experiment was also recorded. To observe the effects of deposit control chemistries, slurries dosed with the acrylic adhesive were also pre-treated with a stickies inhibitor and monitored in the same manner as the untreated experiments.

Protocol B

A specially designed flow cell was used in these experiments. This cell allows measurements to be made on flowing pulp slurries, as to mimic the conditions the sensor undergoes when installed at a paper mill. It is composed of a reserve of pulp slurry in a kettle fitted with a wide propeller stirrer connected to a motor and a drain valve. The valve is connected to a centrifugal pump that drives the flow of stock up through a 55 cm long tubular cell with an inner diameter of 2.6 cm, which has fittings to accommodate three individual QCM sensors and a temperature sensor. Upon exiting the flow cell, the slurry is guided back through a hose to the reserve kettle for recirculation. The deposition and temperature were recorded continuously on all three crystals using the Maxtek RQCM instrument. With this system, data was gathered on pulp slurries with consistencies comparable to the headbox consistency (0.1-0.5%). With three sensors exposed to the same flowing pulp suspension, the effectiveness of different coatings at attracting microstickies could be directly evaluated. To compare the epoxy coating described herein to an uncoated crystal and the polystyrene coating proposed by Tsuji et al. et al., *Method For Measuring Microstickies Using*

*Quartz Crystal Microbalance With Dissipation Monitoring*, Kami Parupu Kenkyu Happyokai Koen Yoshishu 73, 126-129 (2006), the flow cell was fitted with these three sensors and stickies deposition from the flowing pulp slurry was monitored over time. This experiment demonstrated a significant advantage of the proposed method over that described in the literature. In a separate comparative study, the same three crystals were used to monitor deposition from whitewater in place of the flowing pulp slurry.

Protocol C

In this application, the RQCM is fitted to the cell described in Protocol B and is installed in the pulp line or paper/tissue machine (a sidestream connection), to assure a continuous flow of the slurry (mill water). The deposition is recorded continuously as the pulp slurry flows by the faces of the sensors at a rate of 2.0-3.0 gallons per minute (gpm).

Example 1

Figure 2:
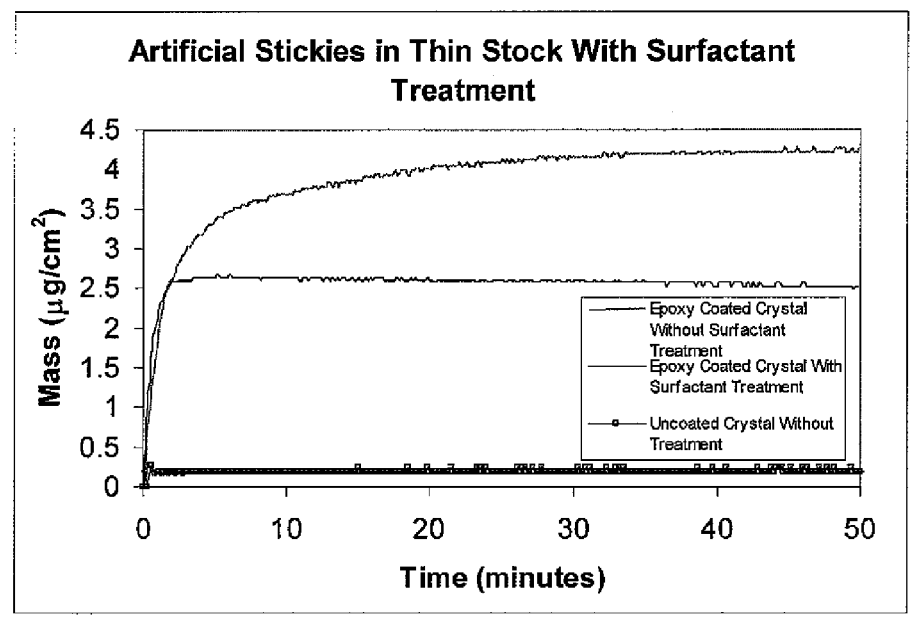
FIG. 2 is a graph that is related to Example 1.

Using the SRM per Protocol A, epoxy-coated crystals were screened for affinity to artificial stickies (acrylic adhesive) in the presence and absence of Nalco chemistries. With no treatment, the artificial stickies accumulated on the epoxy-coated crystal. As shown in FIG. 1 and FIG. 2, in presence of DVP6O002, a surfactant available from Nalco Company, Naperville, Ill., the artificial stickies have no affinity to the epoxy coated crystal.

Figure 3:
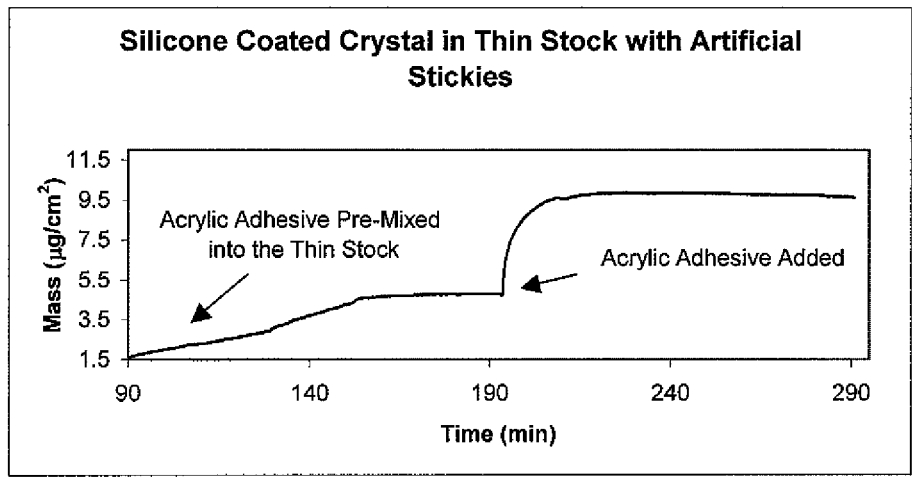
FIG. 3 is a graph that is related to Example 1.
Figure 4:
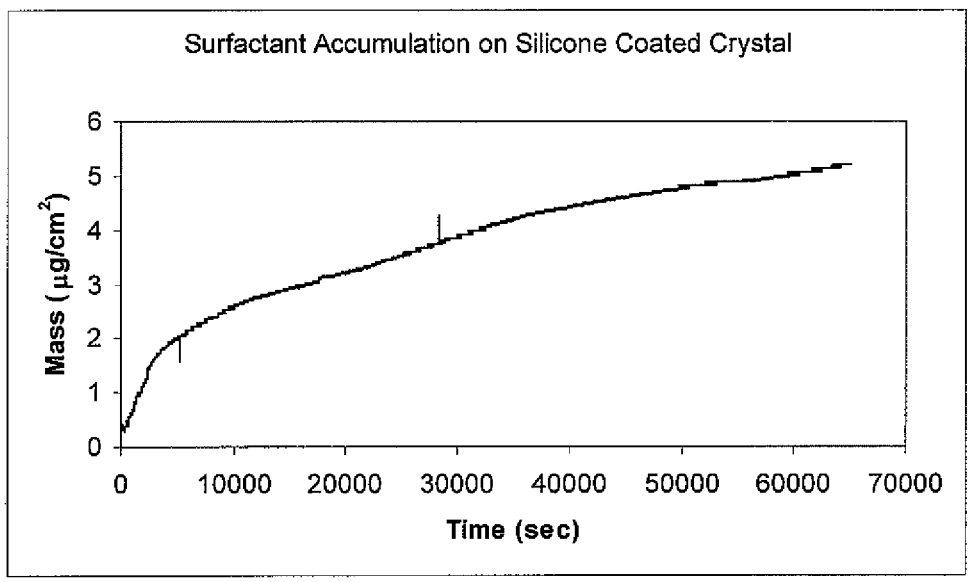
FIG. 4 is a graph that is related to Example 1.

As shown in FIG. 3, a possible alternative to the epoxy, a crystal was coated with room temperature vulcanizing (RTV) silicone, available from Dow Corning Corporation, tested positive for affinity to artificial stickies. In a blank experiment on a dilute pulp slurry containing surfactant DVP6O002, the mass was increasing over time, as shown in FIG. 4. Without surfactant, no mass increase is observed, so the hydrophobic RTV silicone coated crystal appears to be pulling the surfactant out of the slurry.

Figure 5:
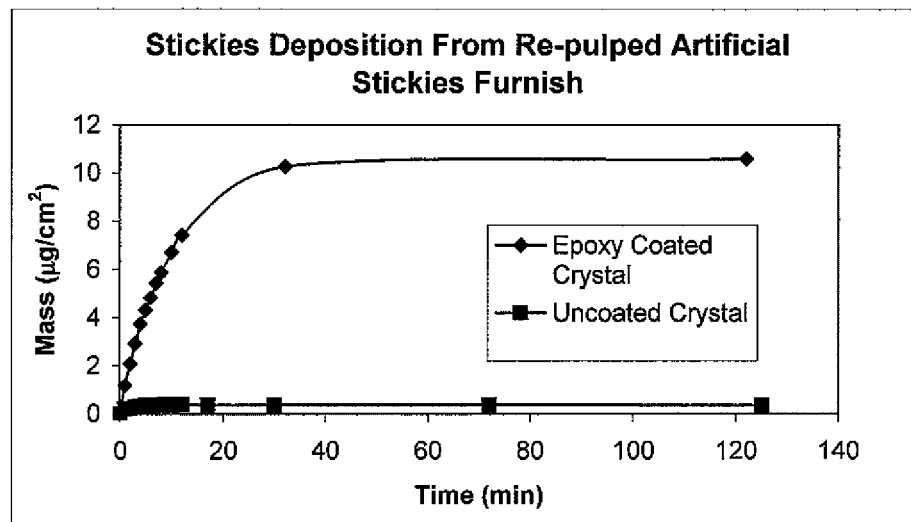
FIG. 5 is a graph that is related to Example 1.

In an attempt to test the crystal coatings for affinity to stickies of different compositions, an artificial stickies furnish was created by re-pulping Post-It® Notes, 3M Corporation, and adhesive labels with plain copy paper. The repulped furnish was diluted to a 0.5% consistency and tested with the epoxy coated and uncoated crystals using the RQCM. As shown in FIG. 5, the epoxy-coated crystal gathered a significantly higher amount of mass ("stickies"). The measurements were taken immediately after the samples came out of the repulper, and the majority of the mass on the crystal was accumulating in the first 30 minutes. To test if this was due to instability of the stickies after high shear forces from re-pulping, the slurry was stirred for 1.5 hours after re-pulping before measuring with the epoxy-coated crystal. A similar trend in deposition was observed, demonstrating the epoxy-coated crystal's ability to detect stickies that are stable in solution.

Example 2

Figure 6:
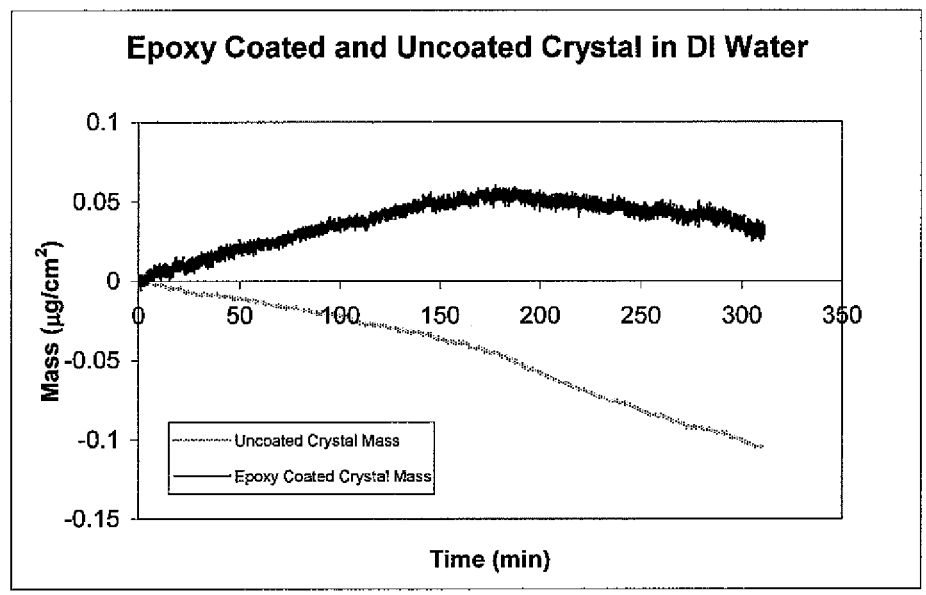
FIG. 6 is a graph that is related to Example 2.

Using Protocol B, the effects of swelling of the polymer coating in an aqueous environment were tested in deionized water and Kraft slurry (0.5% consistency) using the RQCM and the recirculation flow cell. As shown in FIG. 6, the results clearly show that the signal from swelling is minimal in comparison to the deposition observed from microstickies.

Example 3

Figure 7:
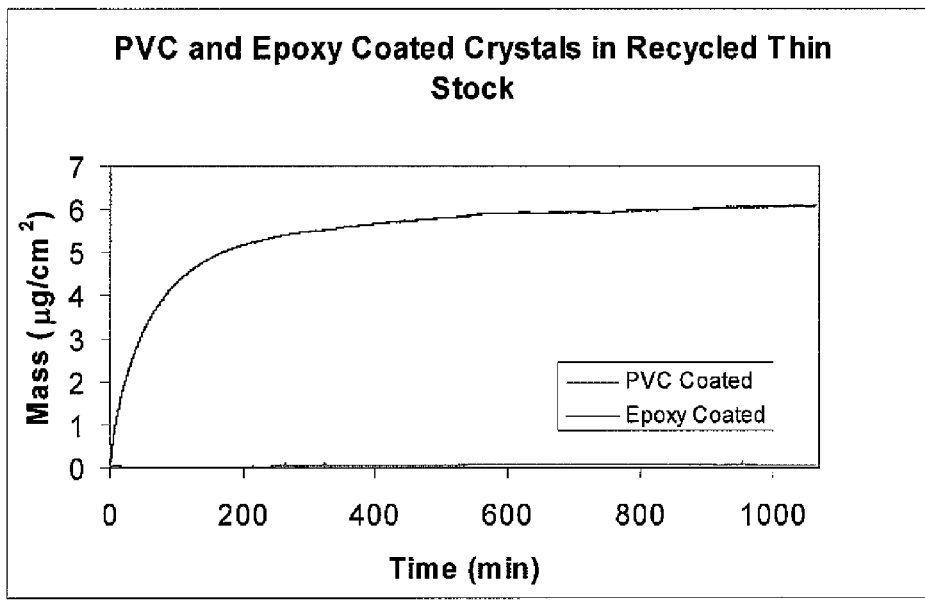
FIG. 7 is a graph that is related to Example 3.
Figure 8:
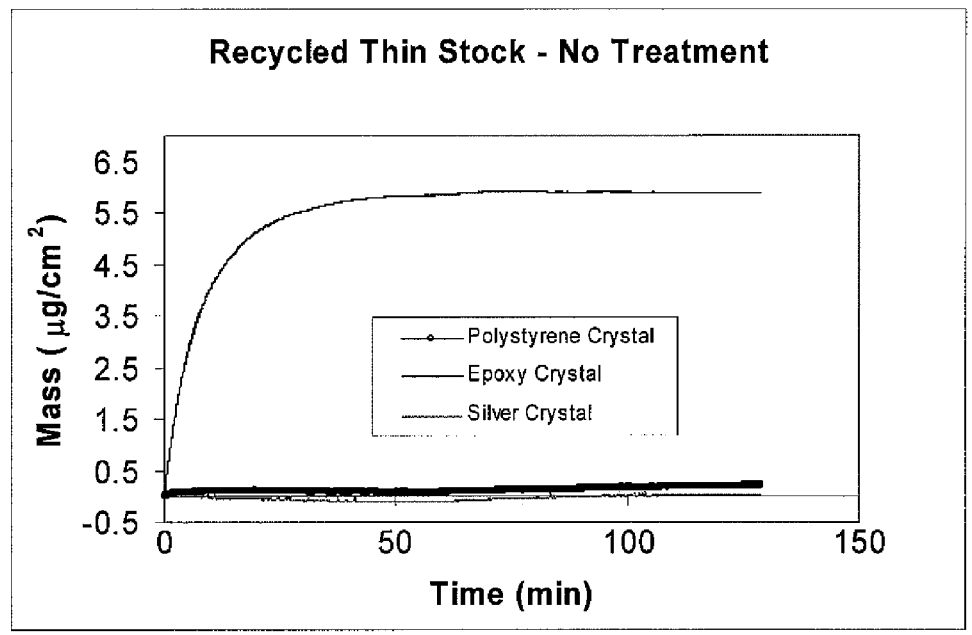
FIG. 8 is a graph that is related to Example 3.
Figure 9:
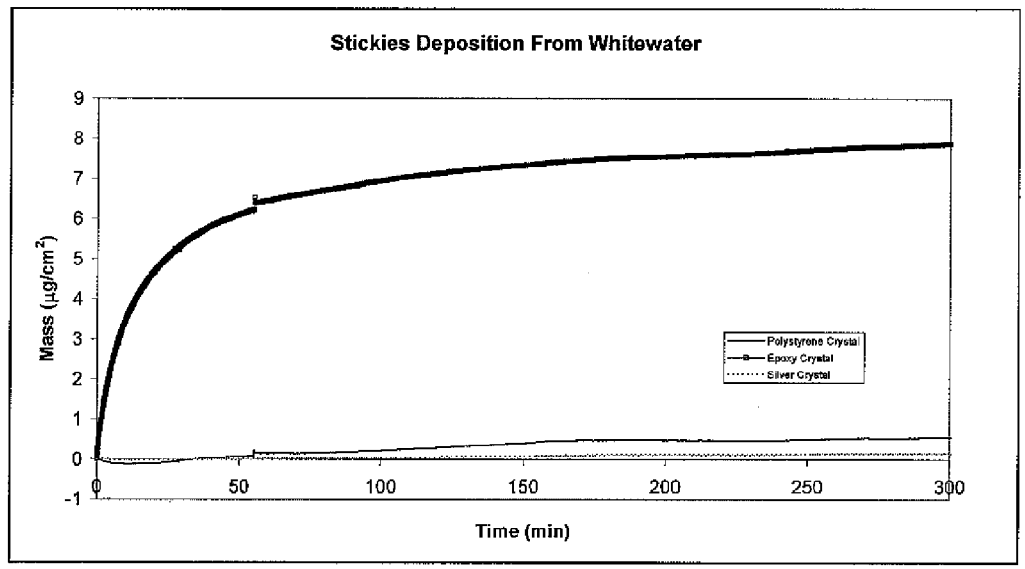
FIG. 9 is a graph that is related to Example 3.

Using Protocol B, coatings were screened for their effectiveness at attracting microstickies. The results are shown in FIGS. 7, 8, and 9. PVC and polystyrene shows no significant response as a coating to attract microstickies in either slurries or the less abrasive whitewater.

Figure 10:
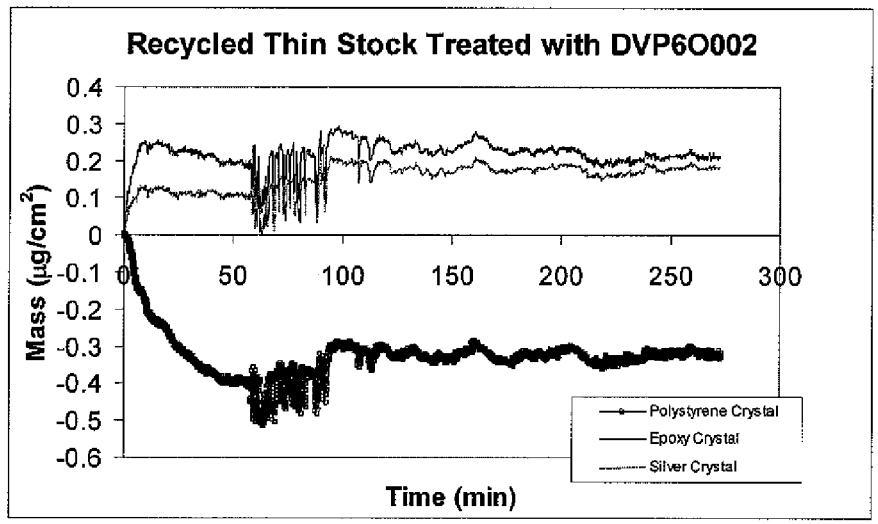
FIG. 10 is a graph that is related to Example 3.

As shown in FIG. 10, pre-treating the slurry with a surfactant before measuring reduces the deposition on the epoxy coated crystal by over 95%.

Example 4

Using the SRM per Protocol A, synthetic pitch accumulation was monitored in a benchtop experiment. A 1% synthetic pitch solution was prepared by mixing 5 g synthetic softwood pitch (a homogenized mixture of 50% abietic acid, 10% oleic acid, 10% palmitic acid, 10% corn oil, 5% oleyl alcohol, 5% methyl stearate, 5% beta-sitosterol, and 5% cholesteryl caproate) in 633 ml iso-propanol. 1 ml of this solution of was added to 10 L of DI water at pH 7.3. A solution of calcium chloride (5000 ppm as Ca ions, 50 ml) was added.

Figure 11:
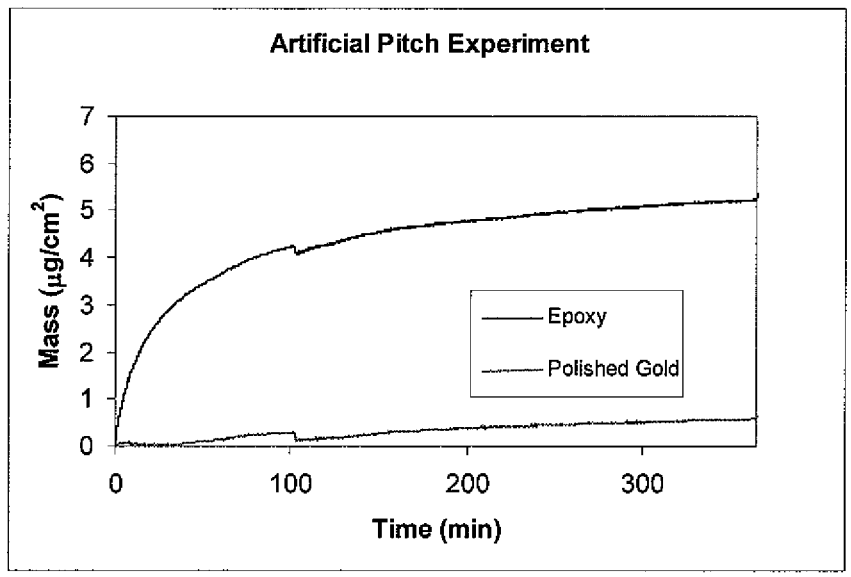
FIG. 11 is a graph that is related to Example 4 and, for comparative purposes, Example 6.

As shown in FIG. 11, compared to the uncoated crystal with a polished gold surface, the epoxy coated crystal has an increased sensitivity for detecting wood pitch in an aqueous environment. Concentration of synthetic pitch was intentionally maintained at a very low level in this experiment. While wood pitch can be monitored using a QCM at high concentrations, it is not so at low concentrations. The experiment shows that the claimed method improves sensitivity of the method, thus making such monitoring possible.

Example 5

Figure 12:
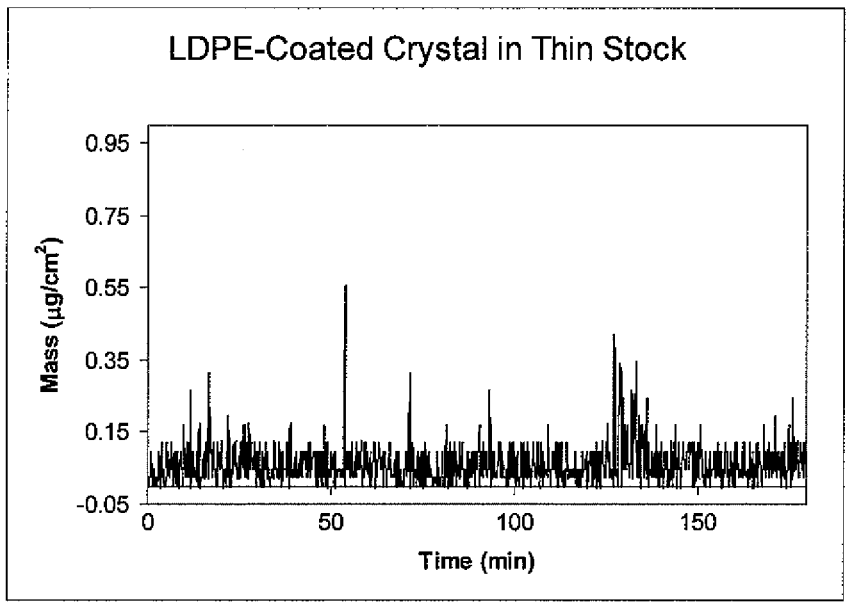
FIG. 12 is a graph that is related to Example 5.

Using the SRM per Protocol A, the low-density polyethylene (LDPE) was also tested as a crystal coating to attract microstickies from recycled furnish. The hypothesis was that the hydrophobic microstickies would be attracted to the highly hydrophobic LDPE coated crystal. The results in FIG. 12 show that this is not the case.

Example 6

Synthetic pitch accumulation was monitored in a benchtop experiment using a DRM setup. A 1% synthetic pitch solution was prepared by mixing 5 g synthetic softwood pitch (a homogenized mixture of 50% abietic acid, 10% oleic acid, 10% palmitic acid, 10% corn oil, 5% oleyl alcohol, 5% methyl stearate, 5% beta-sitosterol, and 5% cholesteryl caproate) in 633 ml iso-propanol.

As shown in Example 4 and FIG. 11, compared to the uncoated crystal with a polished gold surface, the epoxy coated crystal has an increased sensitivity for detecting wood pitch in an aqueous environment. Concentration of synthetic pitch was intentionally maintained at a very low level in this experiment. While wood pitch can be monitored using a QCM at high concentrations, it is not so at low concentrations. The experiment shows that the claimed method improves sensitivity of the method, thus making such monitoring possible.

For Example 6, 1000 ml of 0.5% softwood kraft pulp slurry was placed in a benchtop cell of a DRM instrument (see FIG. 3a in Shevchenko, Sergey M.; Duggirala, Prasad Y.; Deposit management for the bleach plant; IPPTA Journal (2010), 22(1), 135-140). Under mixing, the chemical (3 ml providing 300 ppm product concentration in the sample) and, 5 min later, 100 ml of 1% solution of synthetic softwood pitch (Nalco formulation TX-6226) in iso-propanol were added. Upon homogenization, 5 ml of 5000 ppm (as Ca++ ions) solution of calcium chloride was added and the pH adjusted to 3.5 with dilute hydrochloric acid. The deposit accumulation was recorded using a deposit rate monitor in continuous mode. The same test was done with coated unpolished, uncoated unpolished, and uncoated polished Au/Ti sensor crystals.

Figure 13:
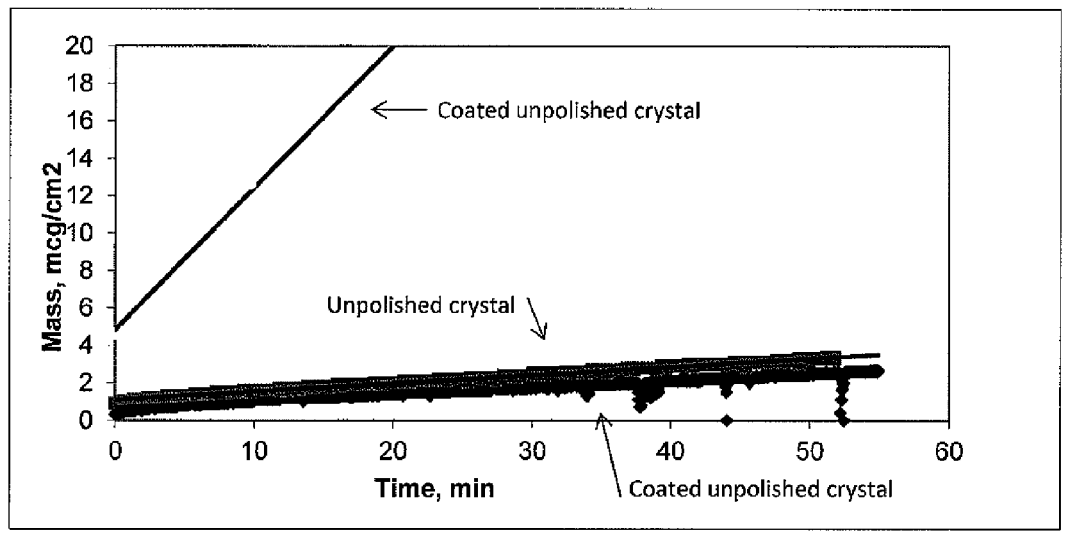
FIG. 13 is a graph that is related to Example 6.

FIG. 13 illustrates accumulation of synthetic pitch in standard benchtop experiments using uncoated and coated crystals. This graph illustrates the difference between the proposed surfaces and surfaces with higher surface energies. The rates illustrated by the lines in FIG. 13 are as follows: Coated: Uncoated unpolished 17:1, Coated:Uncoated polished 21:1, Uncoated unpolished:Uncoated polished 1.25:1. The test shows that the coating provides almost twentyfold increase in sensitivity towards hydrophobic deposits. This is a pitch test, but it can be reasonably assumed that the effect on stickies is similar.

Example 7

Figure 14:
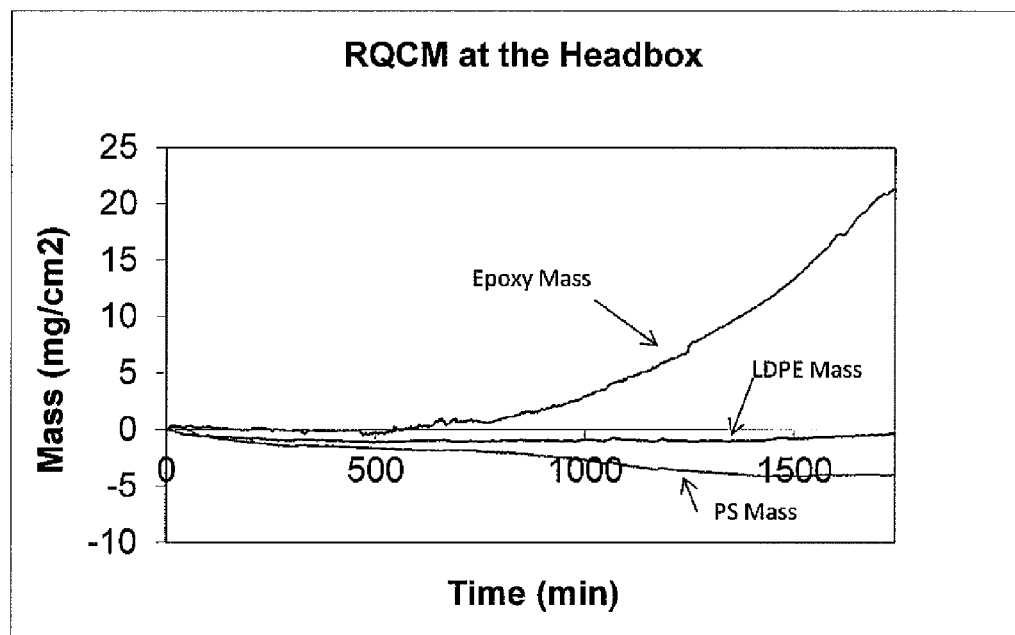
FIG. 14 is a graph that is related to Example 7.

In this application, the on-line DRM instrument was directly connected via a slipstream connection to the pulp line or paper machine to assure a continuous flow of the aqueous pulp slurry. The deposition was recorded continuously as the pulp slurry did flow by the faces of the sensor at a rate of 5.0 gallons per minute (gpm). FIG. 14 illustrates the difference between the proposed surfaces and surfaces with lower surface energies.

What is claimed is:

1. A method for monitoring a rate of deposition of at least one organic material in a papermaking process, the at least one organic material dispersed in an aqueous medium, the monitoring having enhanced sensitivity, the method comprising:
    measuring the rate of deposition of the at least one organic material from the aqueous medium onto a quartz crystal microbalance, wherein the quartz crystal microbalance has a top side and a bottom side,
    wherein the top side contacts the aqueous medium and is coated with a coating material, the coating material having a surface energy in the range from about 34 to about 49 dynes per square centimeter, and
    wherein the bottom side is isolated from the aqueous medium.

2. The method of claim 1 wherein said papermaking process involves recycled pulp and/or broke.

3. The method of claim 1 wherein said organic materials are hydrophobic organic materials, stickies, tackies, white pitch, synthetic contaminants in a papermaking process, wood pitch, natural contaminants in a papermaking process, or a combination thereof.

4. The method of claim 3 wherein said stickies are microstickies.

5. The method of claim 4 wherein said microstickies do not exceed approximately 0.10-0.15 mm.

6. The method of claim 3 wherein said stickies and tackies are selected from the group consisting of: adhesives; coating binders; styrene butadiene rubber; ethylene vinyl acetate; polyvinyl acetate; polyvinyl acrylate; polyvinyl butyral; polybutadiene; wax; alkyd resins; polyol acrylates; and sizing chemicals.

7. The method of claim 1 wherein the top side of the quartz crystal microbalance is made of one or more conductive materials selected from the group consisting of: platinum; titanium; silver; gold; lead; cadmium; diamond-like thin film electrodes with or without implanted ions; silicides of titanium, niobium and tantalum; lead-selenium alloys; mercury amalgams; and silicone.

8. The method of claim 1 wherein said coating material is made of one or more of the materials selected from the group consisting of: epoxy resin, silicone rubber, alkyd enamel, cellulose, polycarbonate, polyester, acrylic polymer, melamine, vinyl resin, nylon, and capron.

9. The method of claim 1 wherein the monitoring occurs in a papermaking process at a location selected from the group consisting of: pulp processing; recycling; a refiner, a repulper; a bleaching chest; a deinking stage; a water loop; a headbox of a paper or tissue machine, and a combination thereof.

10. The method of claim 1 wherein said aqueous medium is a pulp slurry.

11. A method for measuring the effectiveness of inhibitors that decrease a rate of deposition of at least one organic material in a papermaking process, the method comprising:
    a. monitoring the at least one organic material, the at least one organic material dispersed in an aqueous medium, the monitoring comprising measuring the rate of deposition of the at least one organic material from the aqueous medium onto a quartz crystal microbalance, the quartz crystal microbalance having a top side and a bottom side;
    b. adding an inhibitor to the aqueous medium to produce a modified aqueous medium; and
    c. re-measuring the rate of deposition of the at least one organic material from the modified aqueous medium onto the coated surface of the quartz crystal microbalance;
    wherein the top side contacts the aqueous medium and the modified aqueous medium and is coated with a coating material adhered with a coupling agent, the coating material containing a non-swelling epoxy resin or a silicone containing polymer,
    wherein the bottom side is isolated from the aqueous medium and the modified aqueous medium, and
    wherein the inhibitor decreases the deposition of the organic materials from the aqueous medium.

12. The method of claim 11, wherein the coupling agent is a silane compound.

13. A method for measuring the effectiveness of inhibitors that decrease a rate of deposition of at least one organic material in a simulated papermaking process, the method comprising:
    a. monitoring the at least one organic material, the at least one organic material dispersed in an aqueous medium in a simulated papermaking process, the monitoring comprising measuring the rate of deposition of the at least one organic material from the aqueous medium onto a quartz crystal microbalance, the quartz crystal microbalance having a top side and a bottom side;
    b. adding an inhibitor to the aqueous medium to produce a modified aqueous medium; and
    c. re-measuring the rate of deposition of the at least one organic material from the modified aqueous medium onto the coated surface of the quartz crystal microbalance;
    wherein the top side contacts the aqueous medium and the modified aqueous medium and is coated with a coating material adhered with a coupling agent, the coating material containing a non-swelling epoxy resin or a silicone containing polymer,
    wherein the bottom side is isolated from the aqueous medium and the modified aqueous medium, and
    wherein the inhibitor decreases the deposition of the organic materials from the aqueous medium.

14. The method of claim 13, wherein the coupling agent is a silane compound.

* * * * *